(12) United States Patent
Lee et al.

(10) Patent No.: US 12,158,410 B2
(45) Date of Patent: Dec. 3, 2024

(54) REAL-TIME QUANTIFICATION METHOD OF CELL VIABILITY THROUGH SUPRAVITAL DYE UPTAKE USING LENS-FREE IMAGING SYSTEM

(71) Applicants: SOL INC., Seoul (KR); Government of the United States of America, as Represented by the Secretary of Commerce, Gaithersburg, MD (US)

(72) Inventors: Jong Muk Lee, Seoul (KR); Darwin R. Reyes-Hernandez, Clarksburg, MD (US); Brian J. Nablo, Rockville, MD (US)

(73) Assignees: SOL INC., Seoul (KR); Government of the United States of America, as Represented by the Secretary of Commerce, Gaithersburg, MD (US)

(*) Notice: Subject to any disclaimer, the term of this patent is extended or adjusted under 35 U.S.C. 154(b) by 769 days.

(21) Appl. No.: 17/106,961

(22) Filed: Nov. 30, 2020

(65) Prior Publication Data

US 2022/0170842 A1 Jun. 2, 2022

(51) Int. Cl.
| | |
|---|---|
| *G01N 15/1433* | (2024.01) |
| *G01N 15/14* | (2024.01) |
| *G01N 15/1434* | (2024.01) |
| *G01N 33/50* | (2006.01) |

(52) U.S. Cl.
CPC ..... *G01N 15/1433* (2024.01); *G01N 33/5041* (2013.01); *G01N 2015/1452* (2013.01); *G01N 2015/1472* (2013.01); *G01N 2015/1488* (2013.01)

(58) Field of Classification Search
CPC ........... G01N 15/1475; G01N 33/5041; G01N 2015/1452; G01N 2015/1472; G01N 2015/1488; G01N 15/1434; G01N 33/58; G01N 33/583; G01N 2015/1006; G01N 2015/144; G01N 15/1463; G01N 1/30;
(Continued)

(56) References Cited

PUBLICATIONS

"Brian J. Nablo et. al., Live Quantification of Cell Viability Via Neural Red Uptake Using Lens-Free Imaging, National Institute of Standards and Technology, USA, Sol Inc., Korea, 2019" (Year: 2019).*

(Continued)

*Primary Examiner* — Andrae S Allison
*Assistant Examiner* — Phuong Hau Cai
(74) *Attorney, Agent, or Firm* — Studebaker & Brackett PC

(57) ABSTRACT

The present disclosure relates to a real-time quantification method of cell viability through a supravital dye uptake using a lens-free imaging system. The method includes a step of incubating a sample cell in a cell culture medium, steps of detecting light penetrating the cell culture medium and identifying a boundary region of the sample cell at a preset time interval based on the detected light, a step of staining the incubated sample cell with the supravital dye, a step of detecting intensity of light penetrating the cell culture medium at a preset time interval, a step of calculating absorbance of the sample cell included in the cell culture medium at a preset time interval based on the boundary region and the detected intensity of light and a step of analyzing a viability of the sample cell based on the calculated absorbance.

8 Claims, 15 Drawing Sheets

(58) Field of Classification Search
CPC .. G01N 21/31; G01N 21/255; G01N 21/8483; G01N 33/48; C12Q 1/04
See application file for complete search history.

(56) References Cited

PUBLICATIONS

"Gregor Scholz et. al., Continuous Live-Cell Culture Imaging and Single-Cell Tracking by Computational Lensfree Led Microscopy, Sensors 2019, 19[5], 1234, Mar. 2019" (Year: 2019).*

"Joanne Marrison et. al., Ptychography—a label free, high-contrast imaging technique for live cells using quantitative phase information, Scientific Reports 3[1]:2369, PubMed, CC BY-NC-SA 3.0, Aug. 2013" hereinafter as "Marrison" (Year: 2013).*

"DaeHan Ahn et. al., Human-level Blood Cell Counting on Lens-Free Shadow Images Exploiting Deep Neural Networks, Analyst, 2018, 143, 5380, Sep. 2018" (Year: 2018).*

"Jim Clark, Absorbance Measuring the Absorbance of a Solution, Chemguide, Analysis, Mar. 2016" (Year: 2016).*

"Geonsoo Jin et al., Lens-free Shadow Image Based High-Throughput Continuous Cell Monitoring Techniqu, Biosensors and Bioelectronics 38 2012, 126-121, SciVerse ScienceDirect, May 2012" (Year: 2012).*

A. Mazouchi et al., "Fast Optimized Cluster Algorithm for Localizations (FOCAL): a spatial cluster analysis for super-resolved microscopy, Nov. 2015, Bioinformatics, 32-5, 2026, 747-754" hereinafter as "Mazouchi" (Year: 2015).*

* cited by examiner

REAL-TIME QUANTIFICATION METHOD OF CELL VIABILITY THROUGH SUPRAVITAL DYE UPTAKE USING LENS-FREE IMAGING SYSTEM

BACKGROUND

Embodiments of the inventive concept described herein relate to a real-time quantification method of cell viability through supravital dye uptake using a lens-free imaging system.

Determining the viability of cells in the tissue culture within test tubes is an important factor for evaluating the health of cells, the harmfulness of compounds, and the effect of treatment.

The conventional method of evaluating the viability of a cell is generally used as a method of determining the extent to which a supravital dye such as Neutral Red (NR) in the lysosome of a cell is absorbed.

The viability of the cell is determined through a process of extracting the dye absorbed from the dyed cell.

Referring to FIG. 1, the detailed process of the conventional NR absorption analysis method is illustrated.

First of all, the method incubates a cell (S11), and images the cell with an optical microscope (S12).

When the imaging is completed, the method stains the cell (S13) and then incubates the cell again during a predetermined time (S14).

Afterward, the method rinses the cell (S15), images the cell with the optical microscope (S16), extracts a supravital dye from the cell (S17), and quantifies the viability of the cell (S18).

However, the conventional method is somewhat complicated in the above-described procedure. Furthermore, the conventional method includes a destructive post-treatment procedure (S17) of extracting a supravital dye from the stained cell after the staining procedure is completed. In other words, it takes a relatively long time to quantify the absorbance of a cell, and there is a need to essentially include the destructive post-treatment procedure.

Moreover, a preset optical path needs to be formed in an optical microscope used for imaging, and thus the optical microscope has a relatively large volume. Accordingly, for the purpose of imaging cells, it is necessary to take out the cell medium from an incubator and then to observe the cell medium, and thus the procedure for quantification of cell absorbance is delayed, and the equipment required for quantification occupies a relatively large volume.

SUMMARY

Embodiments of the inventive concept provide a time series quantification method capable of quantifying the absorbance of a sample cell without destructive post-treatment for the sample cell.

Furthermore, embodiments of the inventive concept provide a time series quantification method capable of quantifying the absorbance of a sample cell in real time at each moment in a process of incubating and staining the sample cell.

Moreover, embodiments of the inventive concept provide a time series quantification method capable of relatively reducing the volume of equipment required for quantification, using a lens-free imaging system having a relatively small volume.

The technical problems to be solved by the present inventive concept are not limited to the aforementioned problems, and any other technical problems not mentioned herein will be clearly understood from the following description by those skilled in the art to which the inventive concept pertains.

According to an exemplary embodiment, a real-time quantification method of cell viability through a supravital dye uptake using a lens-free imaging system includes incubating a sample cell in a cell culture medium, detecting, by a lens-free image sensor included in the lens-free imaging system, light penetrating the cell culture medium, and identifying a boundary region of the sample cell at a preset time interval based on the detected light, staining the incubated sample cell with the supravital dye, and analyzing, by the lens-free imaging system, a viability of the sample cell by calculating absorbance of the stained sample cell at a preset time interval.

Besides, the analyzing includes detecting, by the lens-free image sensor, intensity of light penetrating the cell culture medium at a preset time interval, calculating the absorbance of the sample cell included in the cell culture medium at a preset time interval based on the boundary region and the detected intensity of light, and analyzing the viability of the sample cell based on the calculated absorbance.

Also, the identifying includes detecting, by the lens-free image sensor, the light penetrating the cell culture medium, and distinguishing the boundary region of the sample cell based on the detected light.

Furthermore, the identifying is performed while a light source, a pinhole filter through which a pinhole capable of penetrating light is formed, the cell culture medium, and the lens-free image sensor are arranged sequentially.

Moreover, the distinguishing of the boundary region includes identifying the boundary region based on a shadow image of the sample cell detected by the lens-free image sensor.

In addition, the detecting of the intensity of light is performed while a light source, a collimator configured to convert incident light into collimated light, the cell culture medium, and the lens-free image sensor are arranged sequentially.

Besides, the detecting of the intensity of light includes detecting, by the lens-free image sensor, first light intensity, which is intensity of light penetrating an inside of the boundary region, and detecting, by the lens-free image sensor, second light intensity, which is intensity of light penetrating an outside of the boundary region.

Also, the calculating includes calculating the absorbance based on a ratio of the first light intensity to the second light intensity.

Furthermore, the method may further include classifying a portion, in which the absorbance is not greater than a preset value, in a portion of the boundary region as a non-overlapping region, and classifying a portion, in which the absorbance is greater than the preset value, in a portion of the boundary region as an overlapping region, before the analyzing of the viability of the sample cell based on the calculated absorbance.

Moreover, the analyzing of the viability of the sample cell based on the calculated absorbance includes analyzing the viability of the sample cell based on the non-overlapping region, the overlapping region, and the absorbance.

Besides, the distinguishing of the boundary region includes classifying a region including an oblong boundary in the boundary region and having an internal area not greater than a preset first area, as a non-overlapping region, and classifying a region including a circular boundary in the boundary region and having the internal area not greater than a preset second area, as an overlapping region. The first area is greater than the second area.

Also, the incubating, the staining, and the analyzing are performed while the lens-free imaging system including the cell culture medium is arranged inside an incubator of a preset environmental condition.

In addition, another method for implementing the inventive concept, another system, and a computer-readable recording medium for recording a computer program for performing the method may be further provided.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
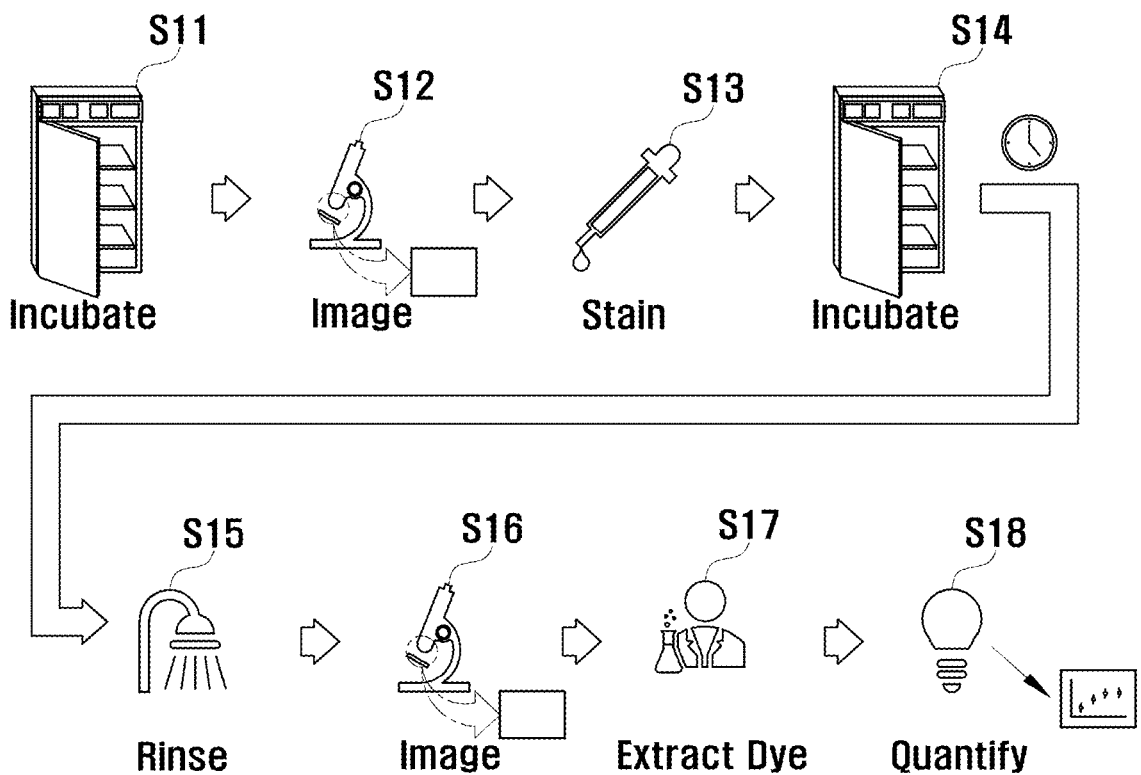
FIG. 1 is a flowchart illustrating the specific process of the conventional NR absorption analysis method.

The above and other aspects, features and advantages of the inventive concept will become apparent from the following description of the following embodiments given in conjunction with the accompanying drawings. The inventive concept, however, may be embodied in various different forms, and should not be construed as being limited only to the illustrated embodiments. Rather, these embodiments are provided as examples so that the inventive concept will be thorough and complete, and will fully convey the concept of the inventive concept to those skilled in the art. The inventive concept may be defined by scope of the claims.

The terminology used herein is for the purpose of describing embodiments and is not intended to limit the inventive concept. In the specification, the singular forms include plural forms unless particularly mentioned. The terms "comprises" and/or "comprising" used herein does not exclude presence or addition of one or more other elements, in addition to the aforementioned elements. The same reference numerals denote the same elements throughout the specification. As used herein, the term "and/or" includes any and all combinations of one or more of the associated components. It will be understood that, although the terms "first", "second", etc., may be used herein to describe various components, these components should not be limited by these terms. These terms are only used to distinguish one component from another component. Thus, a first component discussed below could be termed a second component without departing from the teachings of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Hereinafter, embodiments of the inventive concept will be described in detail with reference to accompanying drawings.

Figure 2:
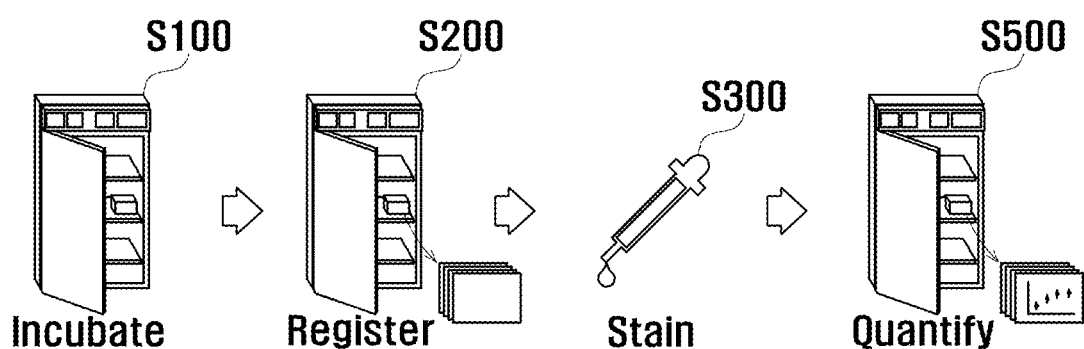
FIG. 2 is a flowchart illustrating a specific process of a cell viability real-time quantification method according to an embodiment of the inventive concept.

Referring to FIG. 2, according to an embodiment of the inventive concept, a time series quantification method of a supravital dye uptake of a cell includes incubating a sample cell in a cell culture medium (S100), identifying a boundary region of the sample cell (S200), staining the incubated sample cell with a supravital dye (S300), and analyzing the viability of the sample cell through a lens-free imaging system 100 (see FIG. 4) (S500).

The analyzing (S500) may be performed after the incubation of the sample cell is started and a preset time elapses. In an embodiment, the analyzing (S500) may be performed after the incubation of the sample cell is started and a preset time elapses. However, it is not limited thereto. The preset time may be differently set depending on the type of a cell to be incubated and the purpose of cell culture.

Furthermore, the analyzing (S500) may be performed for each preset time during the preset time after the staining (S300) is started. In an embodiment, the analyzing (S500) may be performed every hour for 3 hours after the staining (S300) is started. However, it is not limited thereto. The preset time may be differently set depending on the type of a cell to be incubated and the purpose of cell culture. For example, the analyzing (S500) may be continuously performed during a preset time after the staining (S300) is started.

Figure 3:
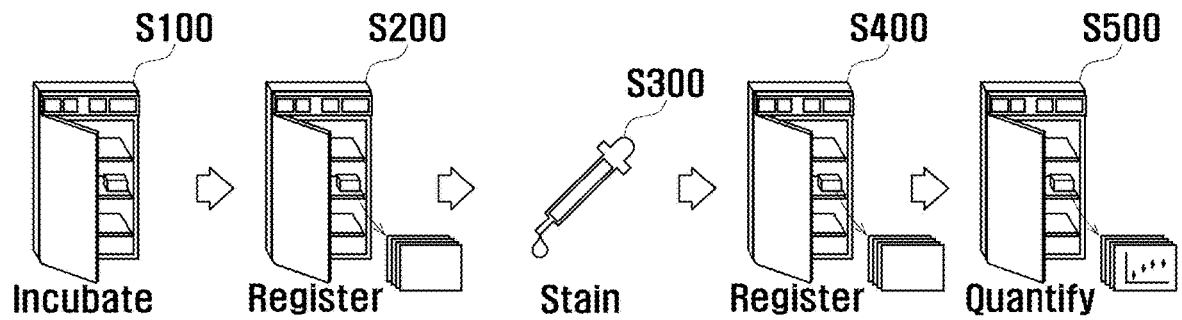
FIG. 3 is a flowchart illustrating a specific process of a cell viability real-time quantification method according to another embodiment of the inventive concept.

Moreover, referring to FIG. 3, the identifying (S400) of a boundary region of the sample cell may be performed between the staining (S300) and the analyzing (S500).

When compared with the above-described identifying (S200) of the boundary region of the sample cell, there is a difference in identifying the boundary region, using the stained sample cell in operation S400.

Hereinafter, the lens-free imaging system 100 performing the above-described operations will be described in detail with reference to FIG. 4.

1. Description of Lens-free Imaging System 100 According to Embodiment of Inventive Concept The lens-free imaging system 100 includes a detection unit 110, a display unit 120, and a database unit 130.

The detection unit 110 is configured to detect a boundary region and an image for measuring the intensity of light by irradiating light onto a cell culture medium.

Besides, an internal space capable of accommodating the cell culture medium including a sample cell is formed in the detection unit 110. Accordingly, the detection unit 110 is disposed in an incubator with the cell culture medium included in the detection unit 110, and the sample cell may be incubated inside the detection unit 110.

Also, the detection unit 110 may be configured to inject a culture medium and a supravital dye into the sample cell with the cell culture medium included therein.

The detection unit 110 includes a light source 111, a pinhole filter 112, an optical filter 113, a collimator 114, and a lens-free image sensor 115.

The configurations of the detection unit 110 may be arranged in the following shape.

First of all, the light source 111, the pinhole filter 112, the optical filter 113, and the lens-free image sensor 115 may be arranged in the first type in which the light source 111, the pinhole filter 112, the optical filter 113, and the lens-free image sensor 115 are arranged sequentially. In the first type, the cell culture medium may be interposed between the optical filter 113 and the lens-free image sensor 115. In the first type, an image for identifying the boundary region of the sample cell is detected. In this regard, it will be described in detail later with reference to FIG. 8.

Besides, the light source 111, the optical filter 113, the collimator 114, and the lens-free image sensor 115 may be arranged in the second type in which the light source 111, the optical filter 113, the collimator 114, and the lens-free image sensor 115 are arranged sequentially. In the second type, the cell culture medium may be interposed between the collimator 114 and the lens-free image sensor 115. In the second type, an image for deriving the intensity of light penetrated through the sample cell is detected. In this regard, it will be described in detail later with reference to FIG. 11.

As the pinhole filter 112 and the optical filter 113 are replaced with the optical filter 113 and the collimator 114, the detection unit 110 may be implemented with a shape transformed from the first type to the second type.

In addition, each configuration of the detection unit 110 functions as follows.

First of all, the light source 111 is configured to irradiate light towards the lens-free image sensor 115. The light source 111 may be designed to irradiate light of the preset intensity. The intensity of light irradiated from the light source 111 may be set differently depending on the type of cell and the purpose of incubation.

The pinhole filter 112 includes a pinhole formed through the pinhole filter 112 in a direction facing the lens-free image sensor 115. The light irradiated from the light source 111 is scattered while penetrating the pinhole and then is directed to the lens-free image sensor 115. Parts other than the pinhole block light from the light source 111 to the lens-free image sensor 115.

The light scattered from the pinhole penetrates the cell culture medium and is incident on the lens-free image sensor 115.

The optical filter 113 is configured to penetrate only the light of a desired predetermined wavelength region. In an embodiment, the optical filter 113 may be configured to penetrate only the light of a region having a wavelength included in 540±35 nm. However, it is not limited thereto, and the preset wavelength region may be set differently.

The collimator 114 is configured to convert the light received from a light source into collimated light facing the lens-free image sensor 115. In an embodiment, most of the light penetrating the collimator 114 may be vertically incident on one side, which faces the light source, in a portion of the lens-free image sensor 115.

The lens-free image sensor 115 is configured to form an image based on light that is irradiated from a light source and then incident on the lens-free image sensor 115. Besides, the lens-free image sensor 115 is configured to detect the intensity of incident light. In an embodiment, the lens-free image sensor 115 may be a Complementary Metal Oxide Semiconductor (CMOS) sensor.

The display unit 120 is configured to provide a user with information about the absorbance of the incubated sample cell and information about the viability of the sample cell calculated based on the absorbance in the visually-recognizable form. In an embodiment, the display unit 120 may not be included in the lens-free imaging system 100. In this case, the information about the absorbance and viability may be transmitted to another device connected to the lens-free imaging system 100 so as to communicate with the lens-free imaging system 100 and then may be displayed separately on the other device. For example, the information about the absorbance and viability may be transmitted and displayed to a terminal (e.g., a mobile phone, PDA, a laptop computer, a computer, or the like) capable of communicating with the lens-free imaging system 100.

The database unit 130 stores images detected by the detection unit 110. Moreover, the information calculated by a controller 140 to be described later is stored in the database unit 130

Also, the database unit 130 may store data and instructions for driving each of configurations of the lens-free imaging system 100.

The database unit 130 may be implemented with a flash memory type, a hard disk type, a solid state disk (SSD) type, a silicon disk drive (SDD) type, a magnetic database unit, a magnetic disk, an optical disk, or the like.

In addition, the database unit 130 may be an external configuration not provided in the lens-free imaging system 100. For example, the database unit 130 may be operated in connection with a web storage that performs a storage function on Internet.

The controller 140 controls the overall operation of the lens-free imaging system 100.

The controller 140 may include a boundary region identification module 141, a light intensity detection module 142, an absorbance calculation module 143, and a viability analysis module 144.

The boundary region identification module 141 receives the shadow image of the cell culture medium detected by the detection unit 110, and specifies the boundary region of the sample cell based on the received shadow image. The boundary region identification module 141 may specify the coordinates of a pixel of the image sensor 115 corresponding to the boundary region of the sample cell. As a result, as described later, the absorbance for each pixel may be calculated.

The shadow image is formed by sensing the light penetrating the cell culture medium disposed in the detection unit 110 in the first type.

Because there is a difference in intensity between the light penetrating the edge of the sample cell and the light penetrating the periphery of the edge of the sample cell, the portion corresponding to the edge of the sample cell is highlighted and displayed in the shadow image. As a result, it is possible to specify a location where a sample cell is arranged, or a boundary region displaying the edge of the sample cell.

Moreover, because the pinhole illumination, which is light that passes through the pinhole filter 112, is used in the first type, the periphery of the sample cell may be displayed darker. Accordingly, the sample cell is displayed more clearly than a portion corresponding to the edge of the sample cell displayed in the shadow image.

As a result, the boundary region of the sample cell may be specified relatively accurately.

The light intensity detection module 142 receives the region image of the cell culture medium detected by the detection unit 110, and detects the intensity of light penetrating the cell culture medium based on the received region image.

The region image is formed by sensing the light penetrating the cell culture medium disposed in the detection unit 110 in the second type.

The light intensity detection module 142 detects the intensity of light, based on the received region image and the boundary region detected by the boundary region identification module 141.

In particular, the light intensity detection module 142 calculates the first light intensity, which is the intensity of the light incident on the lens-free image sensor 115 through the inside of the boundary region, and the second light intensity that is the intensity of light incident on the lens-free image sensor 115 through the outside of the boundary region.

When the boundary region is detected as 'n' individual regions separated from each other, the light intensity detection module 142 calculates the first light intensity for each of the 'n' individual regions.

The absorbance calculation module 143 receives the first light intensity and the second light intensity and then calculates the absorbance for the sample cell.

Besides, the light intensity detection module 142 may calculate information about a light intensity value and absorbance, at preset time intervals during a time specified by a user. Furthermore, the plurality of calculated light intensity values and the calculated absorbance may be used for statistical analysis.

In an embodiment, the standard deviation for values calculated based on a plurality of light intensity values may be derived. The accuracy of the plurality of light intensity values and absorbance may be determined by the derived standard deviation.

In an embodiment, the following equation may be used to calculate the absorbance.

$$A = -\log(I/I_o) \qquad \text{[Equation 1]}$$

A=absorbance
I=first light intensity
$I_o$=second light intensity

That is, the absorbance calculation module 143 calculates the absorbance based on the ratio of the first light intensity to the second light intensity. When light passes through cells that have absorbed the supravital dye, the absorbance is calculated through the amount of light attenuated due to the absorption of light by the cells. As the ratio of the first light intensity to the second light intensity increases, the absorbance decreases; as the ratio decreases, the absorbance increases.

In an embodiment, unlike the above-described embodiment, the second light intensity may be the intensity of light detected by the lens-free image sensor 115 without placing the cell culture medium in the second type of the detection unit 110.

The viability analysis module 144 analyzes the viability of the sample cell based on the calculated absorbance.

In an embodiment, as the viability of the cell is higher, the absorption of supravital dye increases.

The more supravital dye is absorbed, the higher the absorbance of the sample cell may be calculated. Accordingly, the higher the absorbance of the sample cell is calculated, the higher the viability may be analyzed.

Figure 4:
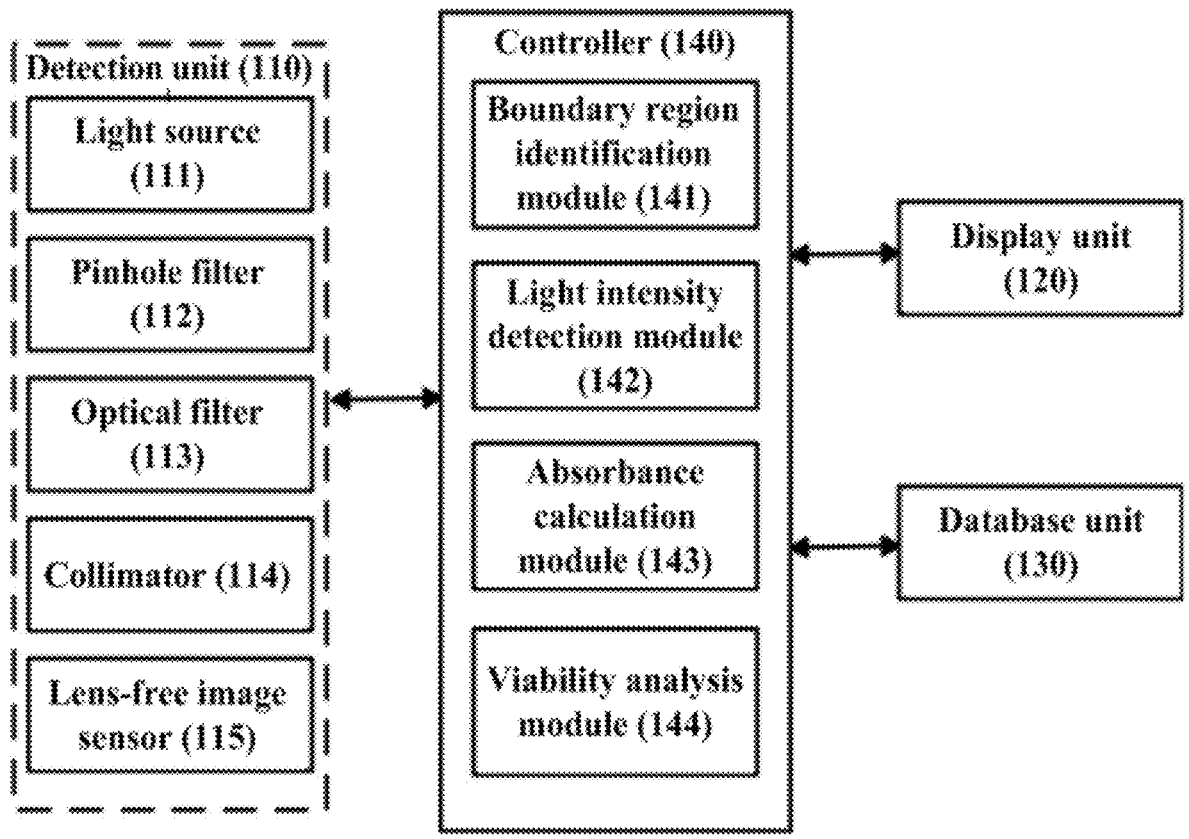
FIG. 4 is a block diagram illustrating a configuration of a lens-free imaging system according to an embodiment of the inventive concept.

However, in some embodiments, the lens-free imaging system 100 may include fewer or more components than the components illustrated in FIG. 4.

For example, the lens-free imaging system 100 may be configured to include only the detection unit 110 and a memory. In this case, information detected by the detection unit 110 is stored in the memory, and viability analysis may be performed by another device receiving the stored information.

2. Description of Real-Time Quantification Method of Cell Viability According to Embodiment of Inventive Concept Hereinafter, the incubating (S100), the identifying (S200), the staining (S300), the identifying (S400) and the analyzing (S500) will be described in detail with reference to FIGS. 6 to 14.

(1) Description of Incubating (S100)

The incubating (S100) includes placing a sample cell in a cell culture medium and incubating the cell culture medium by placing the cell culture medium in an incubator equipped with a preset cell culture environment.

In an embodiment, the sample cell may be a human hepatoma cell (HepG2); the cell culture medium may be Dulbecco's Modified Eagle's Medium (DMEM). The DMEM may include 10% Fetal Bovine Serum.

In an embodiment, the cell culture environment of the incubator may have a temperature of 37 degrees and the carbon dioxide ($CO_2$) concentration of 5%. However, it is not limited thereto. The cell culture environment of the incubator may be differently set depending on the type of a cell to be incubated and the purpose of cell culture.

In an embodiment, the cell culture medium including the sample cell may be accommodated in the lens-free imaging system 100 disposed inside an incubator.

Accordingly, the sample cell may be incubated inside the lens-free imaging system 100.

As time goes on in the preset cell culture environment, the sample cell inside the cell culture medium is incubated.

(2) Description of Identifying (S200)

Figure 7:
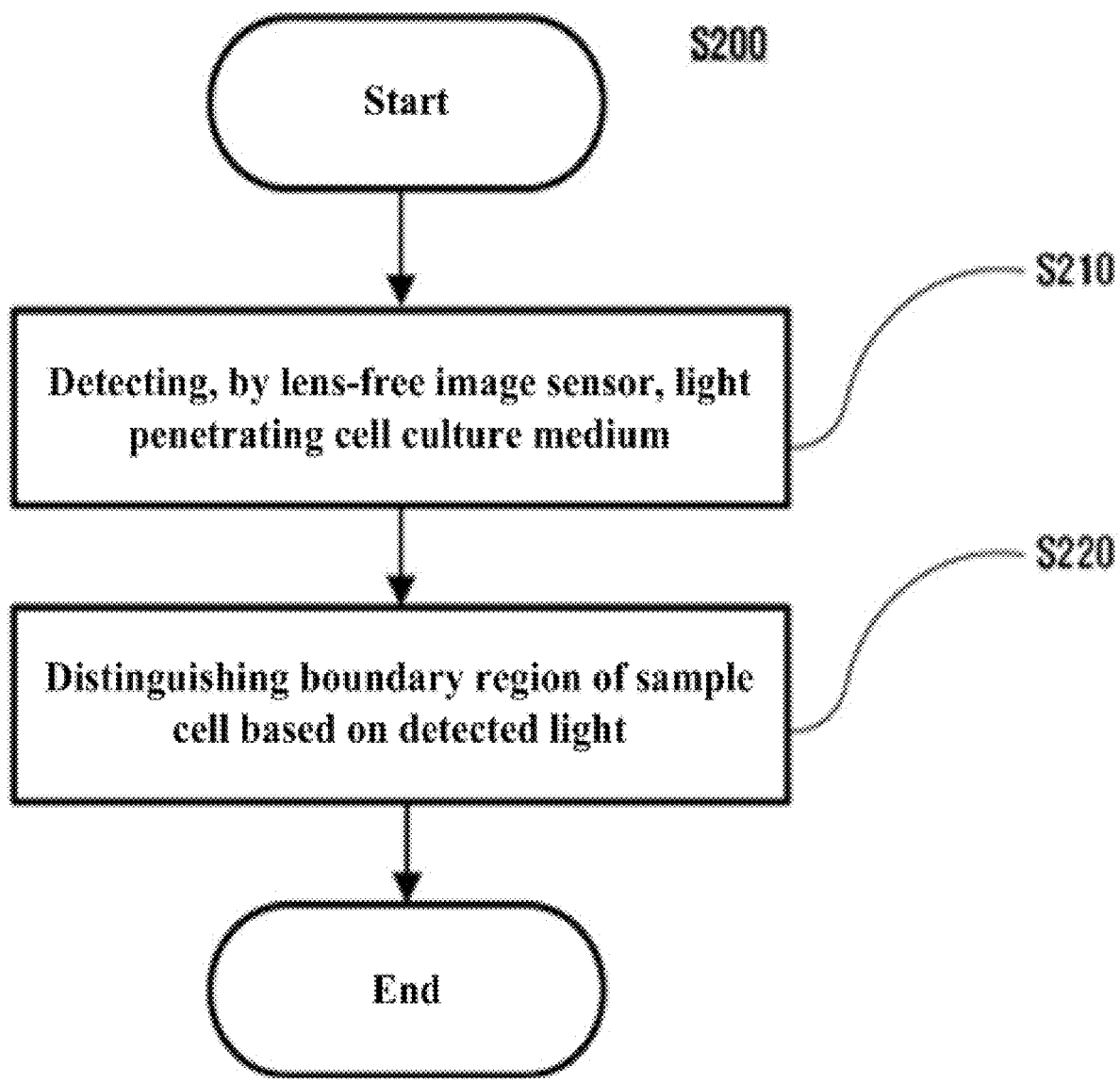
FIG. 7 is a flowchart illustrating a detailed process of an embodiment of operation S200 according to FIG. 5.

Referring to FIG. 7, the process of an embodiment of the identifying (S200) of a boundary region (or Region Of Interest) of a sample cell is illustrated.

First, the identifying (S200) of the boundary region of the sample cell is performed by the detection unit 110 arranged in the first type.

In particular, while the light source 111, the pinhole filter 112, the optical filter 113, the cell culture medium, and the lens-free image sensor 115 are sequentially arranged, the pinhole light scattered through the pinhole is irradiated to the cell culture medium.

Then, the lens-free image sensor 115 detects light penetrating the cell culture medium (S210).

A shadow image is detected based on the detected light, and the lens-free imaging system 100 distinguishes a boundary region based on the detected light (or the shadow image) (S220).

Operation S210 and operation S220 described above may be performed at preset time intervals.

Figure 8:
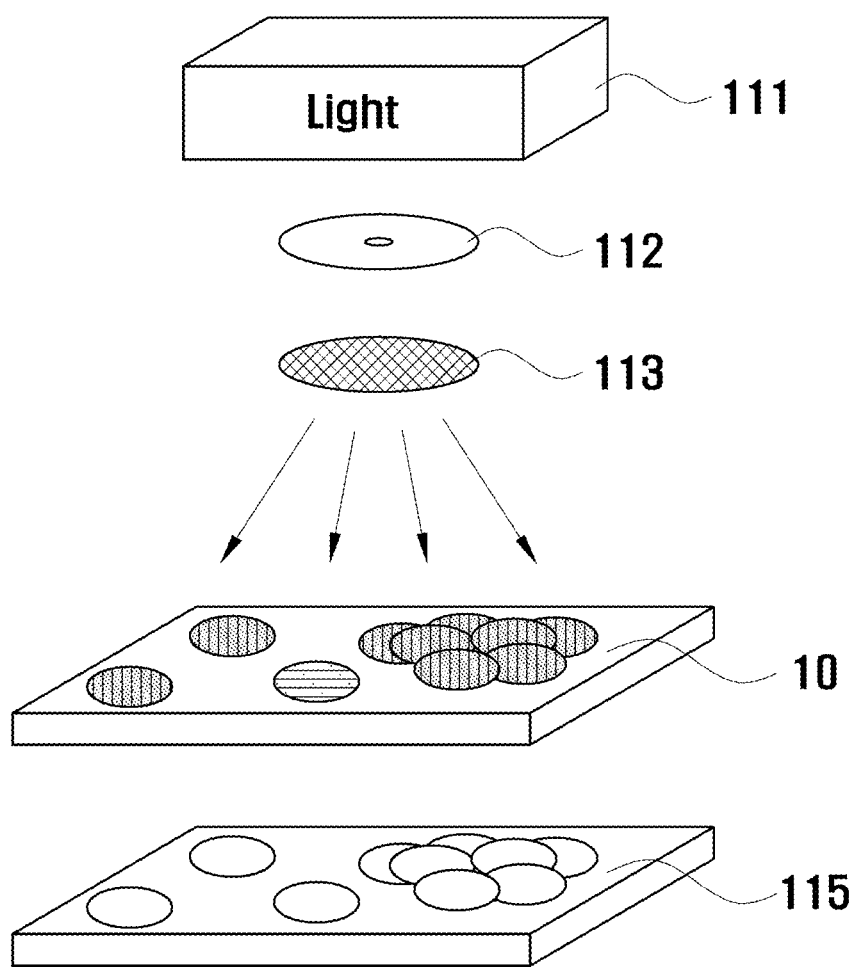
FIG. 8 is a conceptual diagram illustrating an arrangement of some configurations of a lens-free imaging system for performing operation S200 according to FIG. 7.

Referring to FIG. 8, the first type of the detection unit 110 for identifying the boundary region is illustrated.

In the first type, a cell culture medium (10) is interposed between the optical filter 113 and the lens-free image sensor 115. Accordingly, the light source 111, the pinhole filter 112, the optical filter 113, the cell culture medium 10, and the lens-free image sensor 115 are arranged sequentially.

The light irradiated from the light source 111 is scattered in a process of penetrating the pinhole of the pinhole filter 112, and the scattered light penetrates the cell culture medium 10 and then is incident on the lens-free image sensor 115.

Accordingly, a shadow image displayed such that the perimeter of the sample cell is capable of being identified may be detected.

Each of the configurations illustrated in FIG. 8 conceptually illustrates a process in which light irradiated from a light source is incident on the lens-free image sensor 115 to identify a boundary region.

However, FIG. 8 conceptually only illustrates a process in which light penetrates the cell culture medium 10 and then is detected by the lens-free image sensor 115. The shapes of the light source 111, the pinhole filter 112, the optical filter 113, the cell culture medium 10, and the lens-free image sensor 115 are not limited.

For example, an image illustrating the boundary region of cells included in the cell culture medium 10 is illustrated on the upper side of the lens-free image sensor 115. This is to conceptually show a process in which the lens-free image sensor 115 forms an image to identify a boundary region.

In a general optical microscope, a lens for securing an optical path is provided, and the volume of the internal space of the optical microscope is relatively increased to secure the optical path.

On the other hand, the detection unit 110 according to an embodiment of the inventive concept may detect an image through sequentially-arranged configurations without a separate lens and an optical path for identifying an image. Accordingly, the lens-free imaging system 100 according to an embodiment of the inventive concept may be implemented in a relatively small volume compared to the conventional optical microscope.

Figure 9:
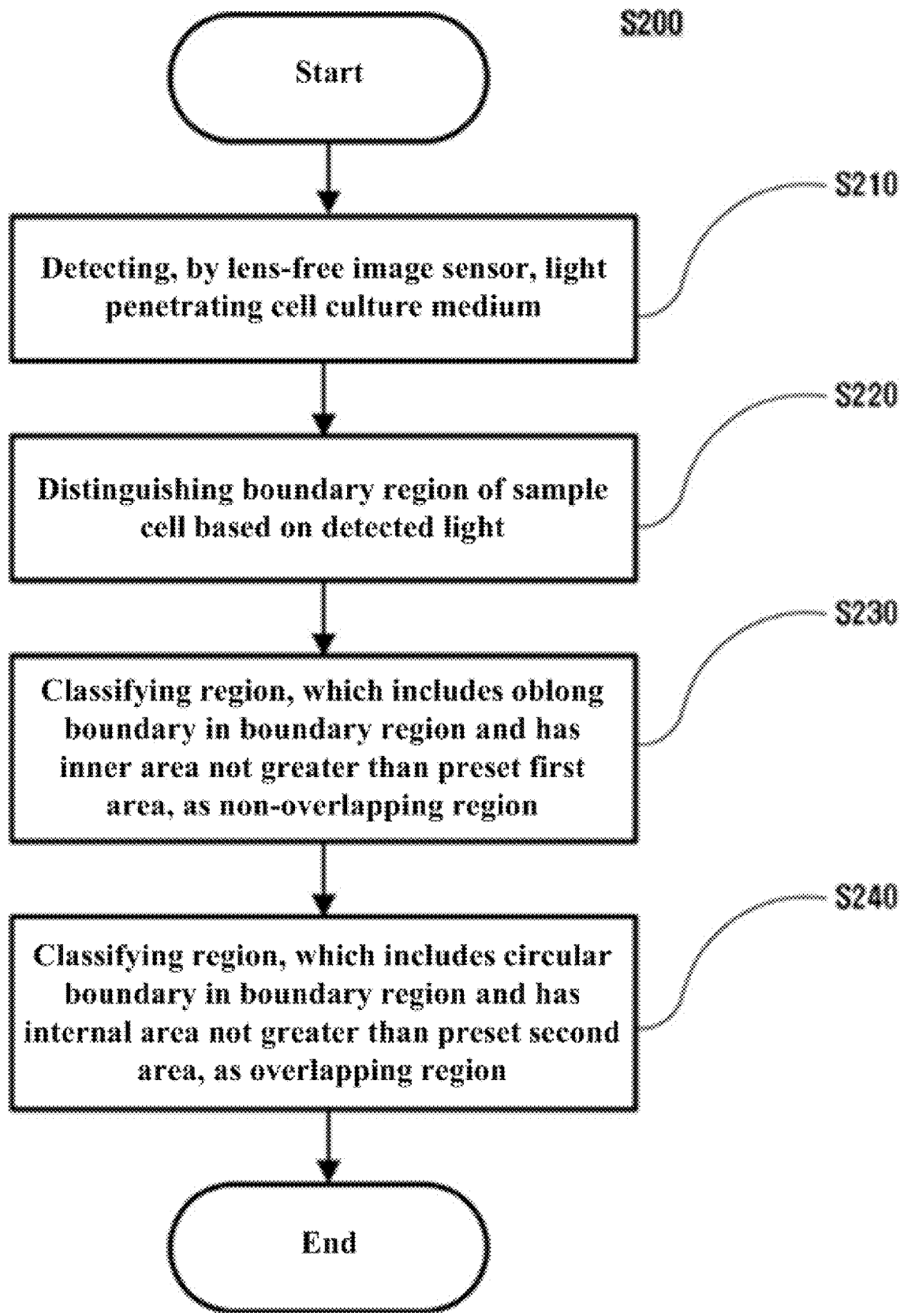
FIG. 9 is a flowchart illustrating a detailed process of another embodiment of operation S200 according to FIG. 5.

Referring to FIG. 9, the detailed process of another embodiment of the identifying (S200) of a boundary region of a sample cell is illustrated.

As compared with the embodiment described with reference to FIG. 7, the identifying (S200) of the boundary region of the sample cell according to an embodiment of the inventive concept has the following difference.

Operation S200 according to an embodiment of the inventive concept further includes classifying a region, which includes an oblong boundary in the boundary region and has an inner area not greater than a preset first area, as a non-overlapping region (S230), and classifying a region, which includes a circular boundary in the boundary region and has an internal area not greater than a preset second area, as an overlapping region (S240).

The incubated sample cells often have an oblong shape. On the other hand, when the incubated sample cells overlap with each other in the direction in which light passes through the sample cells, a portion where the sample cells overlap with each other has a circular shape in many cases. Accordingly, the boundary region may be divided into an overlapping region and a non-overlapping region based on the shape displayed in the shadow image.

The boundary region identification module 141 of the lens-free imaging system 100 may classify a region, which includes an oblong boundary in the boundary region and has an internal area not greater than a preset first area, as the non-overlapping region. In an embodiment, the first area may be 665 $\mu m^2$.

Moreover, the boundary region identification module 141 of the lens-free imaging system 100 may classify a region, which includes a circular boundary in the boundary region, and has an internal area not greater than a preset second area, as the overlapping region. In an embodiment, the second area may be 91 $\mu m^2$.

When the sample cells overlap in the light transmission direction, the overlapping area is reduced more than the area of a single sample cell, the second area is set smaller than the first area.

(3) Description of Staining (S300)

When the incubation of a sample cell is started and the preset time elapses, a supravital dye is supplied to the sample cell incubated during a preset time.

A Neutral Red (NR) dye may be used as the supravital dye. However, it is not limited thereto, and various types of supravital dyes may be used.

When the supravital dye is supplied and time elapses, the incubated sample cell absorbs some of the supravital dye and is stained. Until the supravital dye is absorbed into the incubated sample cell at a saturated concentration, the absorption of the supravital dye increases as time goes on.

(4) Description of Identifying (S400)

After the staining S300, the identifying S400 may be performed additionally. As compared with the above-described identifying (S200), the identifying (S400) of a boundary region in a state where the sample cell is stained is performed.

The specific process is the same as the above-described identifying (S200), and thus a redundant description will be omitted.

(5-1) Description of Analyzing (S500) According to Embodiment

Figure 5:
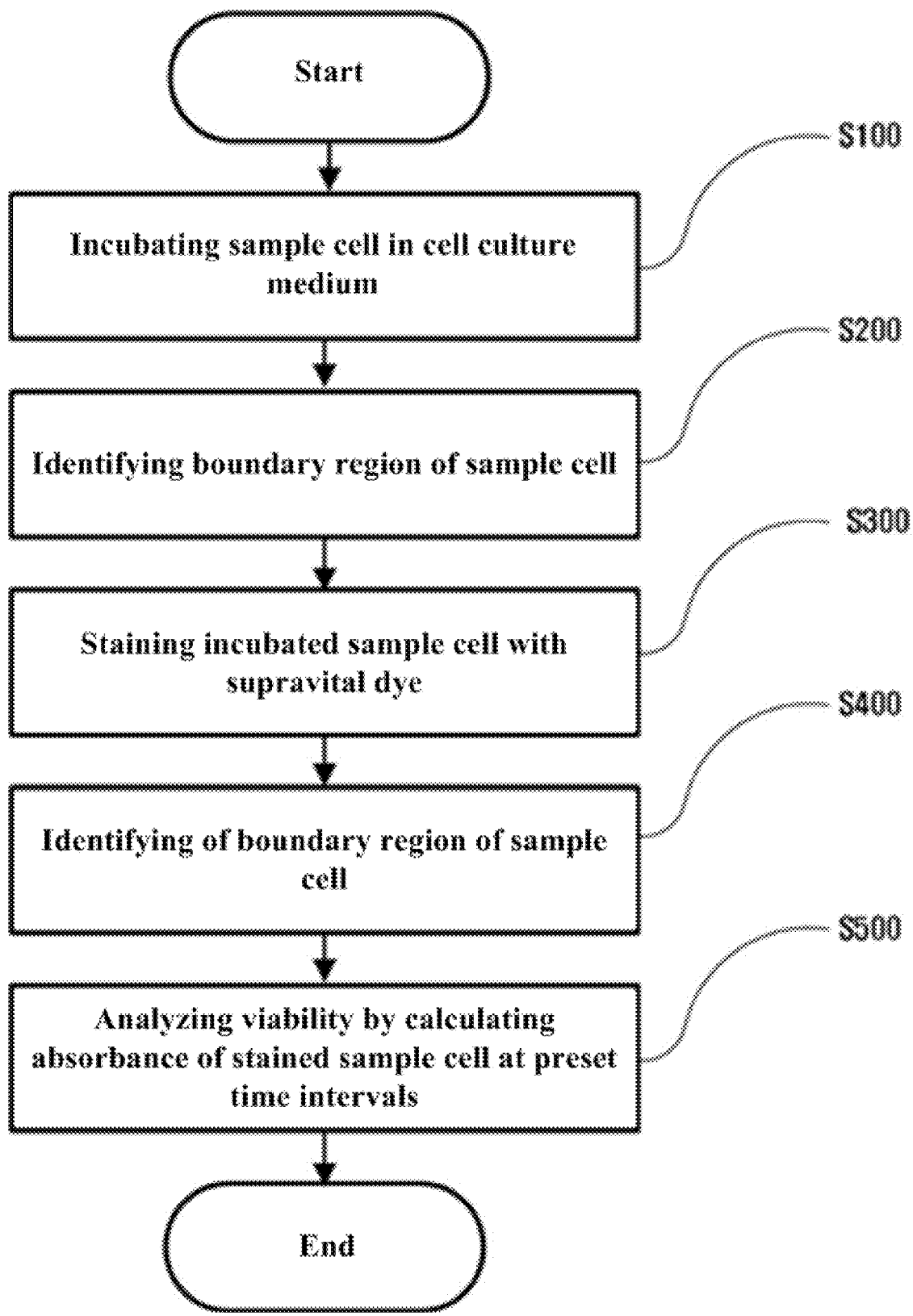
FIG. 5 is a flowchart illustrating a specific process of a cell viability real-time quantification method according to another embodiment of the inventive concept.
Figure 10:
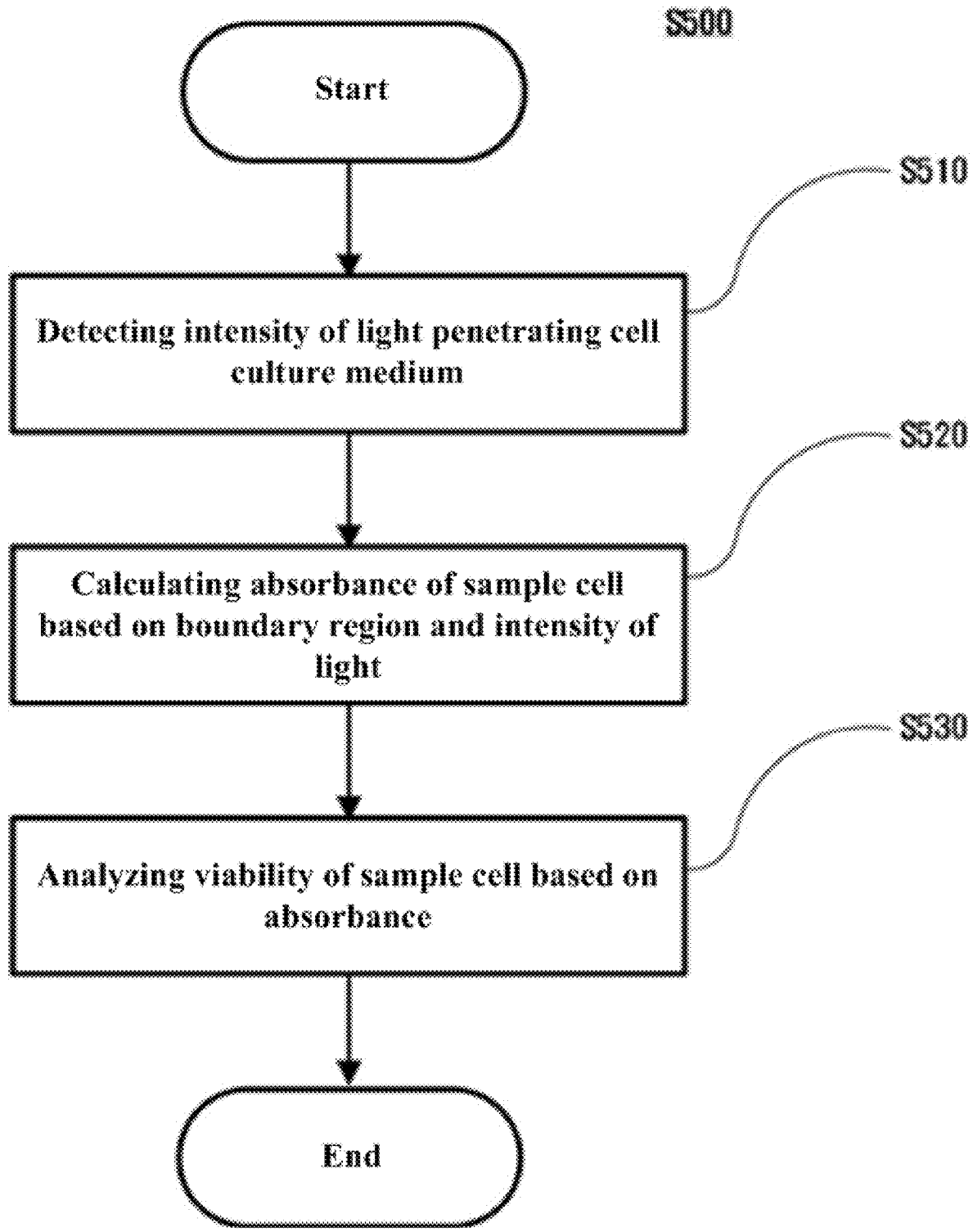
FIG. 10 is a flowchart illustrating a detailed process of an embodiment of operation S500 according to FIG. 5.

Referring to FIG. 10, a detailed process of an embodiment of operation S500 according to FIG. 5 is illustrated.

First of all, the analyzing (S500) includes detecting the intensity of light penetrating a cell culture medium (S510), calculating the absorbance of the sample cell based on a boundary region and the intensity of light (S520), and analyzing the viability of the sample cell based on the calculated absorbance (S530).

In particular, the absorbance of the sample cell is calculated by specifying the boundary region, which is the region in which the sample cell cultured in the cell culture medium is placed, and detecting the intensity of light penetrating the inside of the boundary region and the intensity of light penetrating the outside.

As the amount of supravital dye absorbed into the sample cell increases, the intensity of light penetrating the boundary region of the sample cell is reduced. Accordingly, the absorbance of the sample cell may be calculated based on the ratio of the intensity of light penetrating the inside and outside of the boundary region.

The boundary region of the incubated sample cell may be composed of a plurality of regions spaced apart from one another.

In addition, incubated samples cell may be disposed partially overlapped with one another in a direction in which light penetrating the incubated samples, and thus a plurality of small regions constituting the boundary region of the sample cell may include different shapes.

Figure 6:
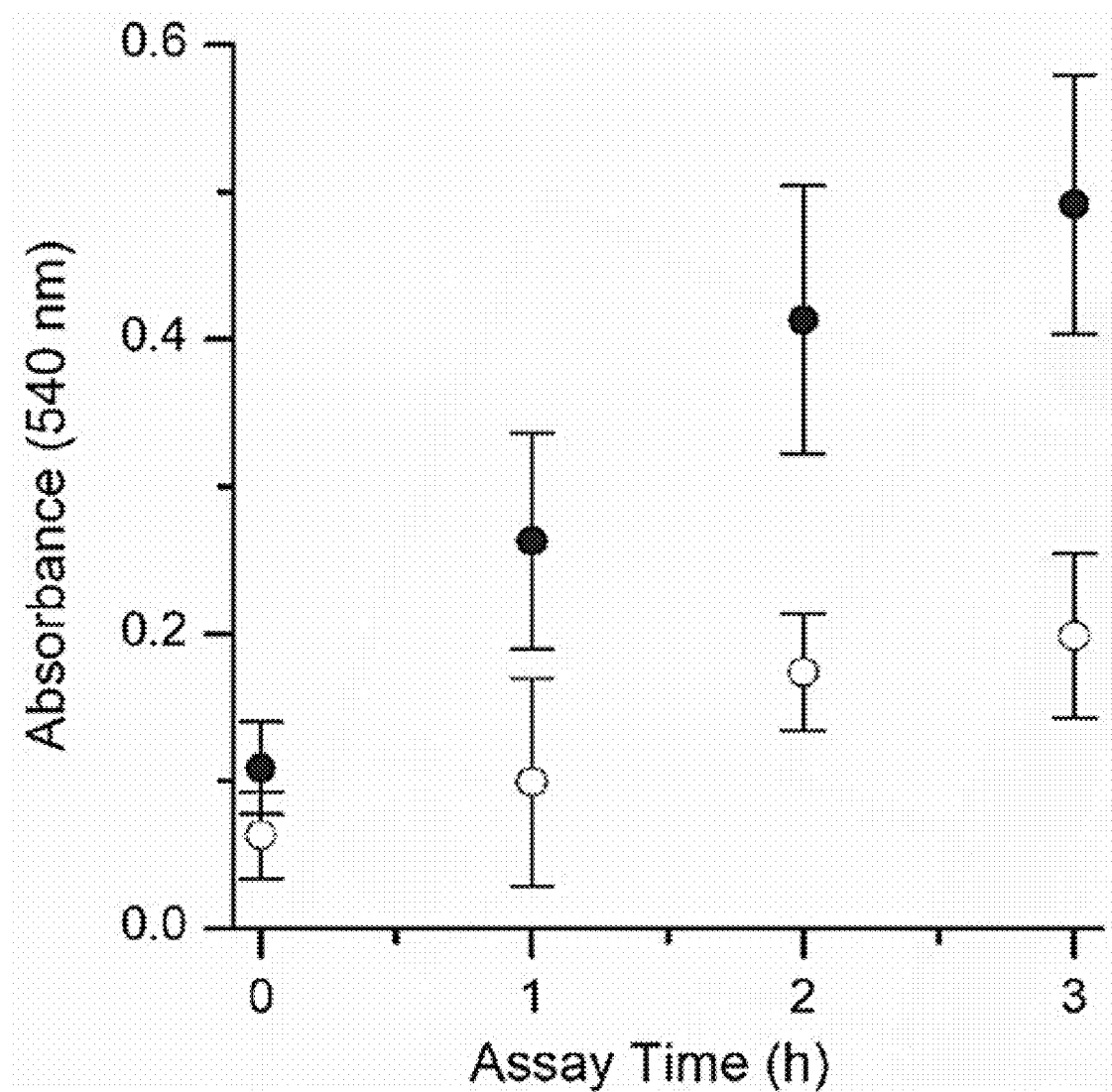
FIG. 6 is a graph illustrating absorbance calculated depending on operation S500 of FIG. 5.

Referring to FIG. 6, the absorbance of the sample cell calculated at an interval of 1 hour is illustrated.

The absorbance has been plotted as a box plot expressed with a maximum value (max), a minimum value (min), and a median value (median).

The upper box plot, which is placed on the upper side and in which the median value (median) is expressed as a solid circle (closed), may mean the absorbance in the boundary region where sample cells overlap with one another.

The lower box plot, which is placed on the lower side and in which the median value (median) is expressed as a hollow circle (open), may mean the absorbance in the boundary region where sample cells do not overlap with one another.

The absorbance is calculated to be higher as the sample cells overlap, and thus it may be seen that the absorbance in the boundary region where the sample cells overlap with one another is measured to be higher.

Also, the amount of supravital dye absorbed into a sample cell increases as time goes on, and thus it may be seen that the absorbance increases in a time-series manner.

In the lens-free imaging system 100 described above, the above-described boundary region may be specified, and the intensity of light may be detected.

Referring to FIG. 10, the detailed process of detecting (S510) the intensity of light penetrating a cell culture medium is illustrated.

To measure the intensity of light penetrating a sample cell, the illumination of collimated light, which is converted into the collimated light through a collimator, is irradiated to the cell culture medium in the detection unit 110 arranged in the second type.

That is, while the light source 111, the optical filter 113, the collimator 114, the cell culture medium, and the lens-free image sensor 115 are sequentially arranged, the collimated light is irradiated to the cell culture medium.

When the collimated light is irradiated, the lens-free image sensor 115 detects the intensity of light penetrating the cell culture medium (S510).

A region image is detected based on the detected light, and the lens-free imaging system 100 detects the intensity of light based on the detected region image.

Operation S510 described above may be performed at preset time intervals.

Figure 11:
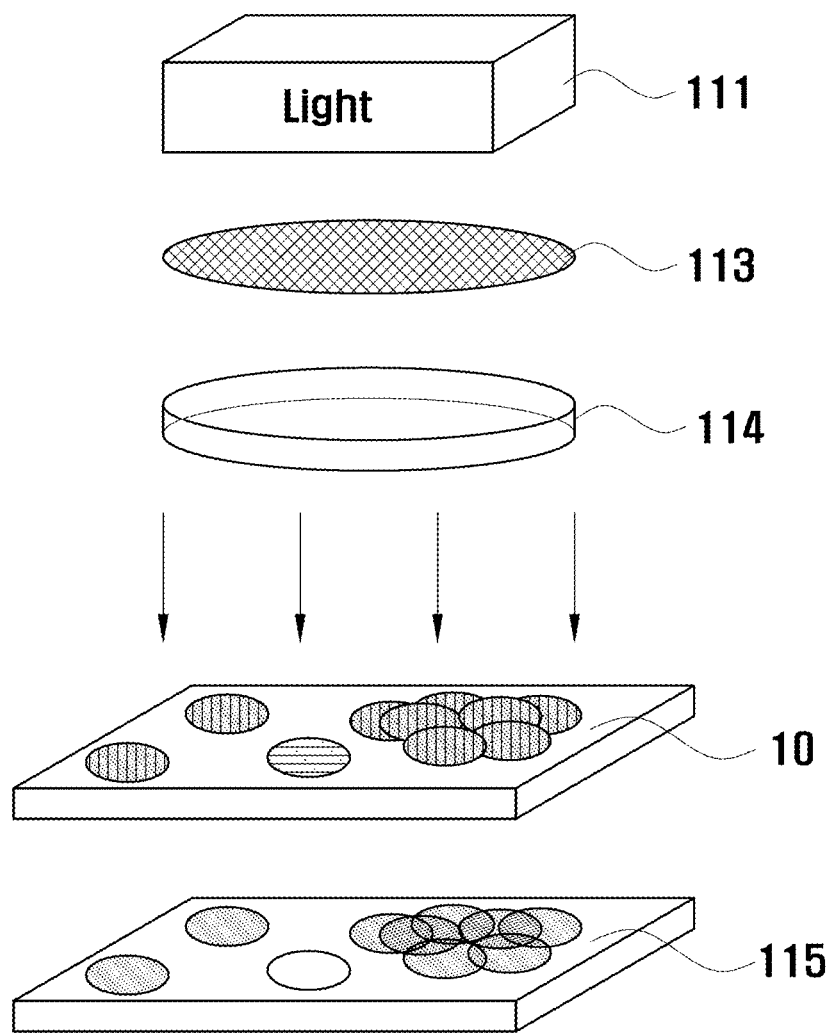
FIG. 11 is a conceptual diagram illustrating an arrangement of some configurations of a lens-free imaging system for performing operation S510 according to FIG. 10.

Referring to FIG. 11, the second type of the detection unit 110 for detecting the intensity of light is illustrated.

In the second type, the cell culture medium 10 is interposed between the optical filter 113 and the lens-free image sensor 115. Accordingly, the light source 111, the optical filter 113, the collimator 114, the cell culture medium 10, and the lens-free image sensor 115 are arranged sequentially.

The light irradiated from the light source 111 is converted into collimated light in a process of penetrating the collimator 114, and the converted light penetrates the cell culture medium 10 and then is incident on the lens-free image sensor 115. Accordingly, a region image may be detected.

Each of the configurations illustrated in FIG. 11 conceptually illustrates a process in which light irradiated from a light source is incident on the lens-free image sensor 115 to measure the intensity of light penetrating the cell culture medium 10 to the inside and outside of the boundary region.

However, FIG. 11 conceptually only illustrates a process in which light penetrates the cell culture medium 10 and then is detected by the lens-free image sensor 115. The shapes of the light source 111, the optical filter 113, the collimator 114, the cell culture medium 10, and the lens-free image sensor 115 are not limited.

For example, an image illustrating the intensity of light penetrating the cell culture medium 10 is displayed for each region on the upper side of the lens-free image sensor 115. However, the image displayed on the upper side of the lens-free image sensor 115 conceptually shows that the intensity of light penetrating the cell culture medium 10 is changed depending on whether to penetrate a sample cell, the viability of a sample cell, whether sample cells overlap with one another, or the like.

As the inner color of a circle shown on the upper side of the lens-free image sensor 115 is darker, it means that the intensity of detected light is weak. Besides, the intensity of light penetrating a sample cell having low viability is detected relatively strongly, and the intensity of light penetrating a portion where sample cells overlap with one another is detected relatively weakly.

In a general optical microscope, a lens for securing an optical path is provided, and the volume of the internal space of the optical microscope is relatively increased to secure the optical path.

On the other hand, the detection unit 110 according to an embodiment of the inventive concept may detect an image through sequentially-arranged configurations without a separate lens and an optical path for identifying an image. Accordingly, the lens-free imaging system 100 according to an embodiment of the inventive concept may be implemented in a relatively small volume compared to the conventional optical microscope.

Figure 12:
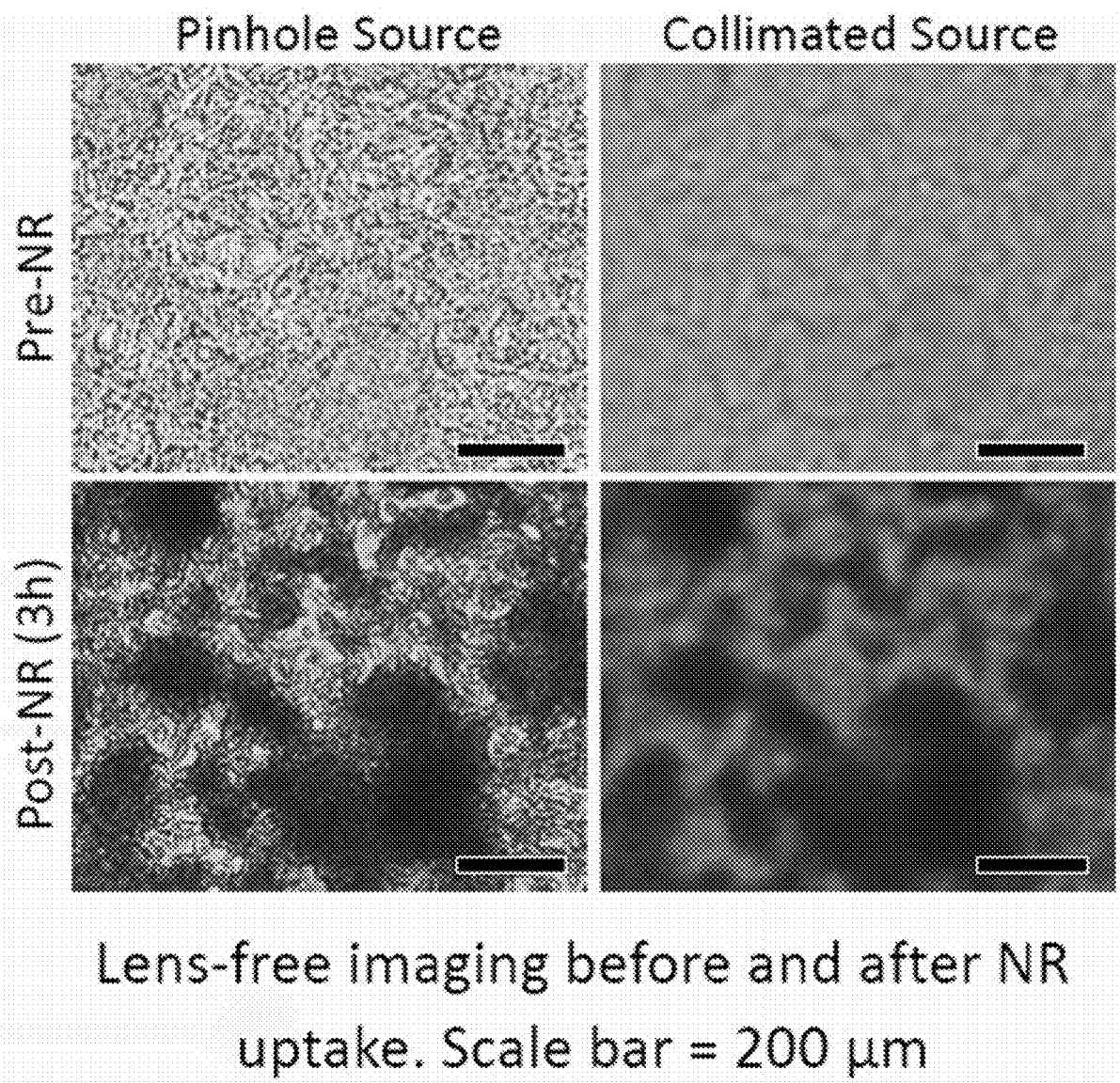
FIG. 12 is a diagram illustrating an image detected by a lens-free image sensor in operation S200 and operation S500 according to FIG. 5.

Referring to FIG. 12, the shadow image detected by the first type of the detection unit 110 and the region image detected by the second type of the detection unit 110 are displayed.

The image positioned on the upper side is the image detected before a supravital dye is stained; the image positioned on the lower side is the image detected after 3 hours later after the supravital dye is supplied.

Figure 13:
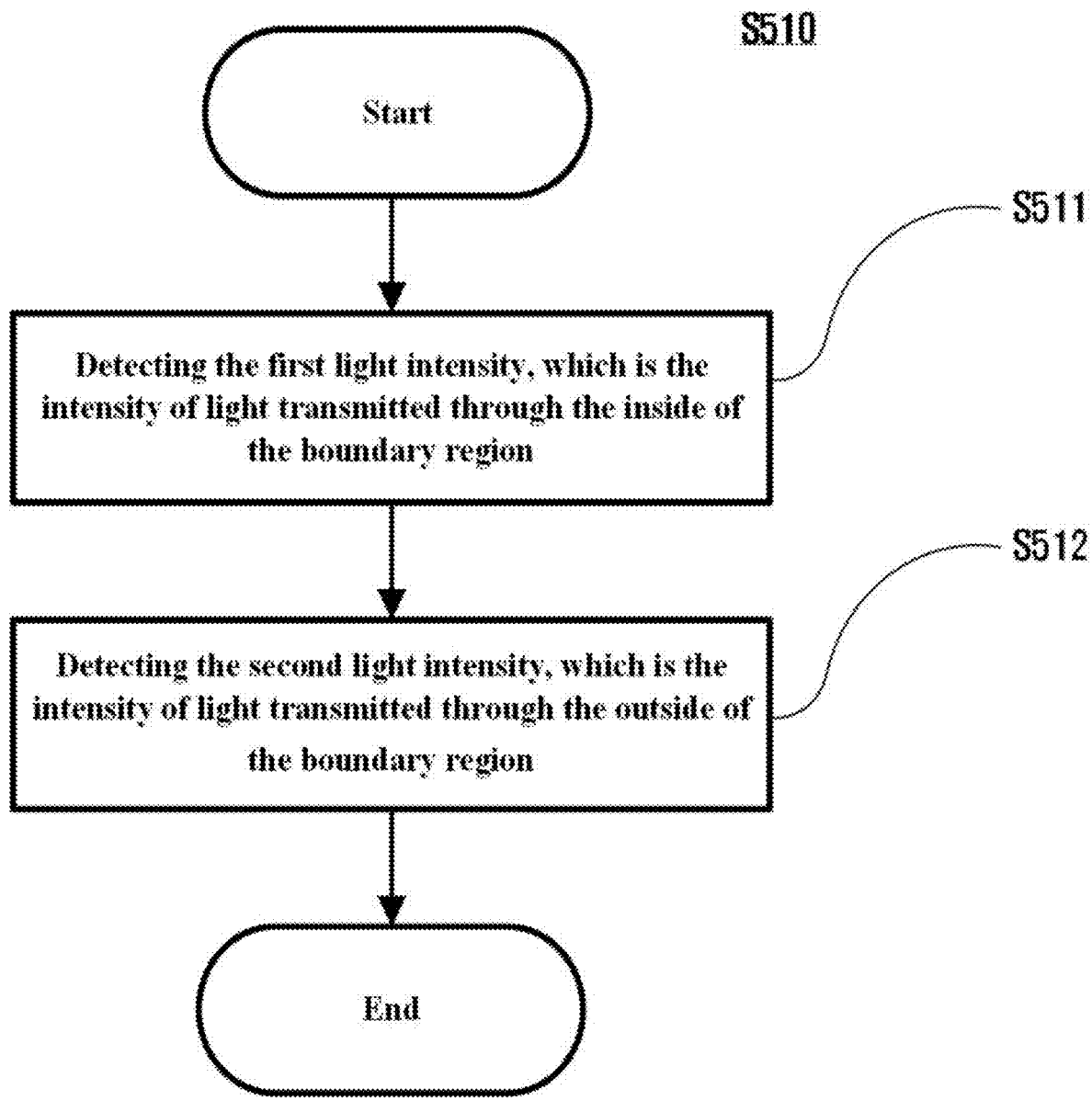
FIG. 13 is a flowchart illustrating a detailed process of operation S510 according to FIG. 10.

Referring to FIG. 13, the detailed process (S510) in which the lens-free image sensor 115 detects the intensity of light penetrating a cell culture medium is illustrated.

First of all, the lens-free image sensor 115 detects first light intensity, which is the intensity of light penetrating the inside of the boundary region (S511), and detects second light intensity, which is the intensity of light penetrating the outside of the boundary region (S512).

The lens-free imaging system 100 calculates the absorbance of the sample cell based on the detected first light intensity and the detected second light intensity (S520).

When the absorbance is calculated, the lens-free imaging system 100 analyzes the viability of the sample cell based on the calculated absorbance (S530).

The lens-free imaging system 100 may be composed of only the detection unit 110 and a memory. In this case, the detecting (S510) of the intensity of light penetrating the cell culture medium is performed by the lens-free imaging system 100, and remaining operation S520 and operation S530 may be performed by a separate processing device.

(5-2) Description of Analyzing (S300) According to Another Embodiment

Figure 14:
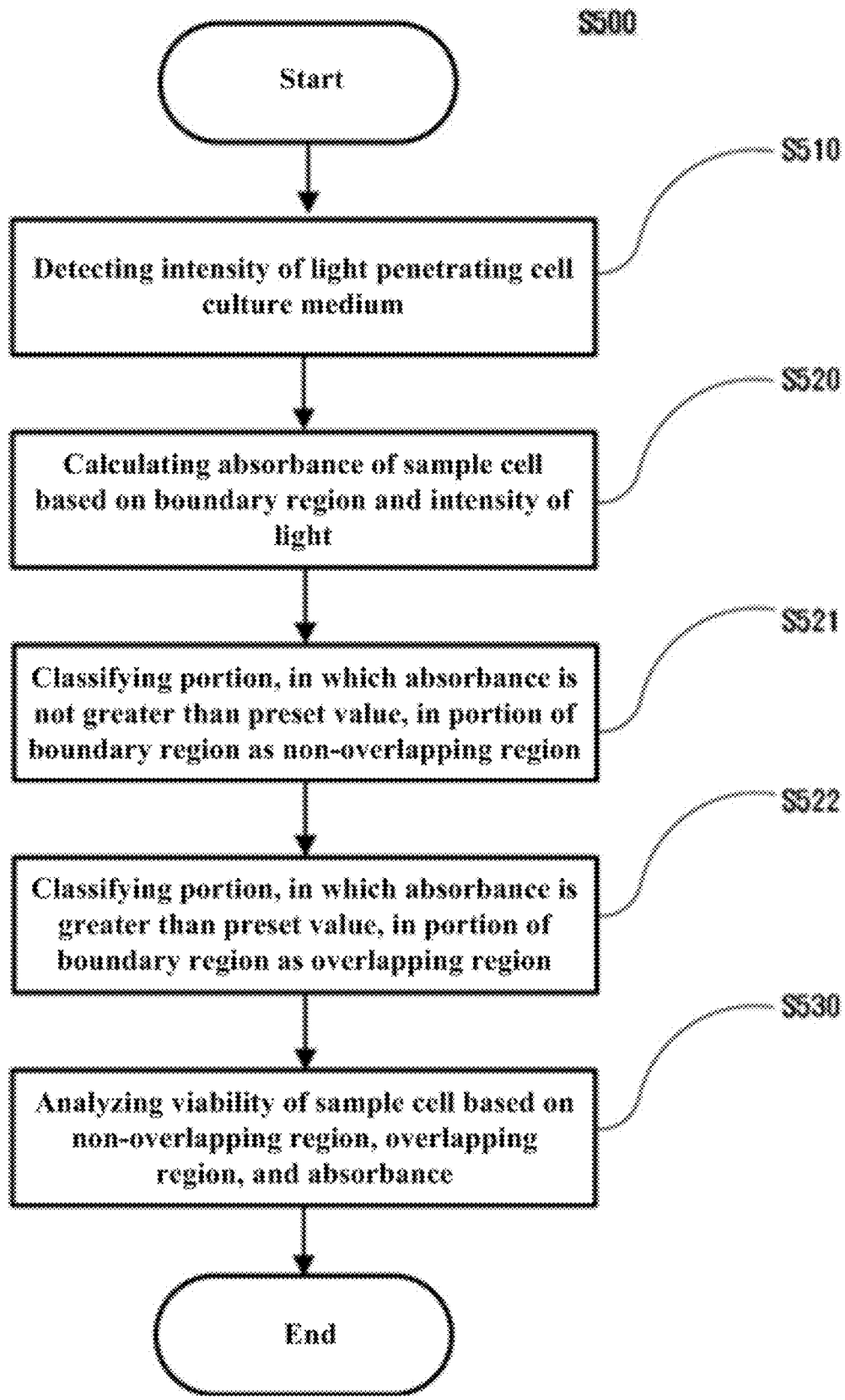
FIG. 14 is a flowchart illustrating a detailed process of another embodiment of operation S500 according to FIG. 5.

Referring to FIG. 14, the detailed process of the analyzing (S500) according to another embodiment is illustrated.

As compared with the embodiment described with reference to FIG. 10, the analyzing (S500) according to an embodiment of the inventive concept has the following difference.

The analyzing (S500) according to an embodiment of the inventive concept further includes classifying (S521) a portion, in which the absorbance is not greater than a preset value, in a portion of the boundary region as a non-overlapping region, and classifying (S522) a portion, in which the absorbance is greater than the preset value, in the portion of the boundary region as an overlapping region.

Furthermore, the viability of the sample cell is analyzed based on the non-overlapping region, the overlapping region, and the absorbance (S530).

When a region from which the viability of the sample cell is derived is a non-overlapping region, the derived viability value refers to the viability of the sample cell of the corresponding region; when a region from which the viability of the sample cell is derived is an overlapping region, the derived viability value refers to the viability for a plurality of sample cells.

Accordingly, the viability value in the overlapping region may be corrected in consideration of an overlap degree. For example, when it is determined that two cells overlap with each other, the viability of the sample cell included in the overlapping region is multiplied by ½ as a correction value.

In an embodiment, the preset value may be set based on the absorbance of non-overlapping sample cells.

Figure 15:
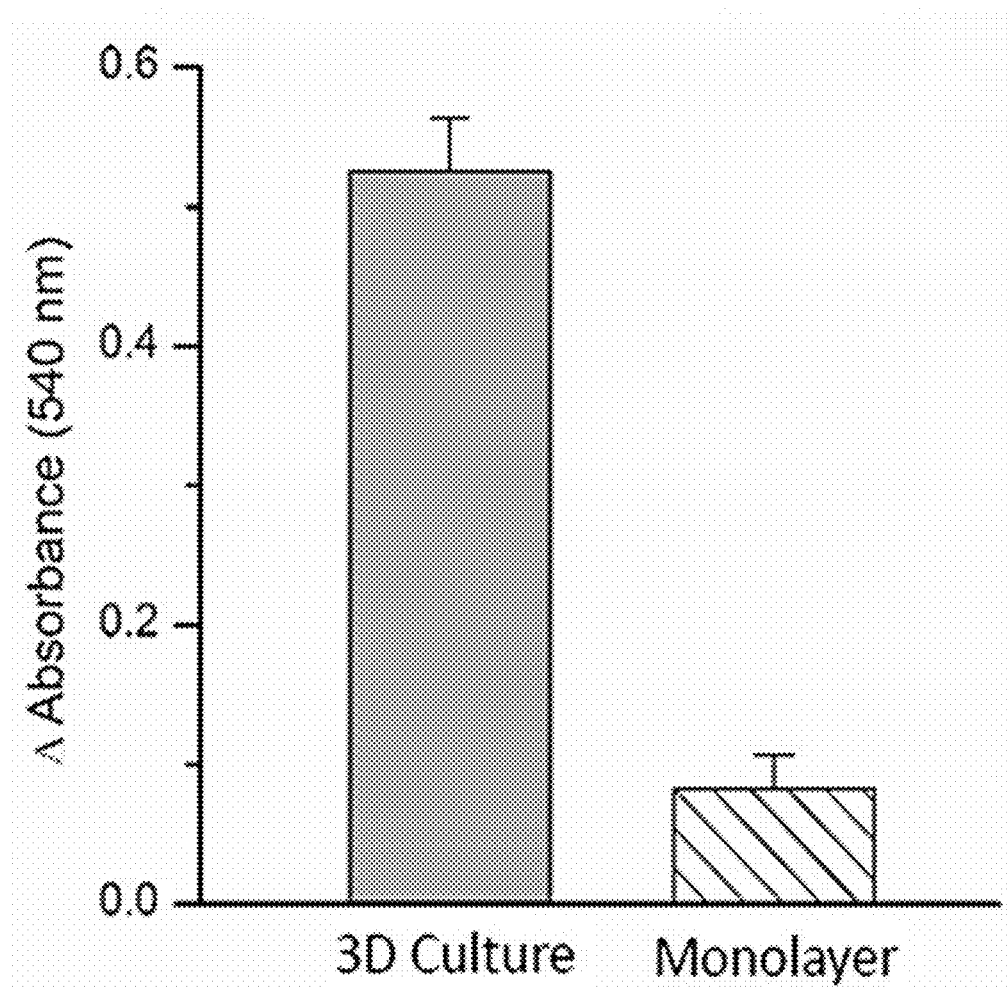
FIG. 15 is a graph illustrating absorbance in an overlapping region and absorbance in a non-overlapping region.

Referring to FIG. 15, the absorbance of the overlapped sample cells is measured to be higher than that of the non-overlapping sample cell. In this way, a preset value capable of distinguishing non-overlapping sample cells may be set, and an overlapped region and a non-overlapping region may be distinguished based on the preset value.

In an embodiment not illustrated, the lens-free imaging system 100 may calculate the overlap degree of individual regions constituting the boundary region, based on the calculated absorbance of the boundary region.

In an embodiment, after a plurality of sequential sections are set, the overlap degree corresponding to the corresponding section may be assigned to the boundary region having the absorbance corresponding to each section. For example, the overlap degree of 1 may be assigned to the boundary region having the absorbance included in the 10~20 sections; the overlap degree of 2 may be assigned to the boundary region having the absorbance included in the 20~30 sections.

A 3D image may be implemented based on the calculated overlap degree and the image detected by the detection unit 110.

Figure 16:
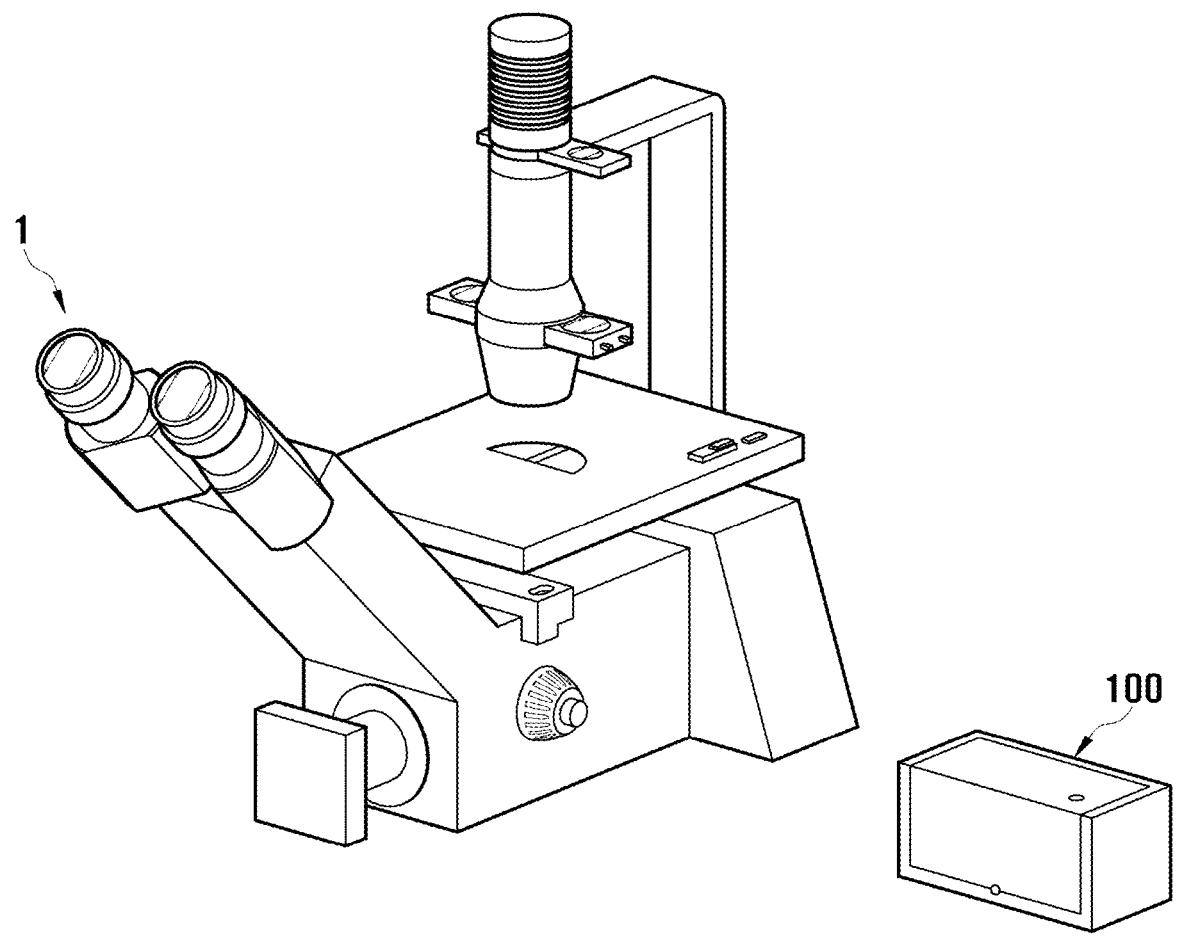
FIG. 16 is a perspective view illustrating a conventional optical microscope and a lens-free imaging system of the inventive concept.

3. Description of Effect of Time Series Quantification Method of Supravital Dye Uptake of Cell According to Embodiment of Inventive Concept Referring to FIG. 16, a conventional optical microscope 1 and the lens-free imaging system 100 of the inventive concept are shown.

A conventional optical microscope 1 has a relatively large volume due to a lens and an optical path. On the other hand, the lens-free imaging system 100 according to an embodiment of the inventive concept has a relatively small volume.

Besides, the absorbance may be calculated by irradiating light to a cell culture medium positioned inside the lens-free imaging system 100, without destructive additional procedures such as extracting a dye from a cell.

Moreover, incubation, boundary region identification, staining and viability quantification processes may be performed in a state where the cell is included in the lens-free imaging system 100. That is, according to an embodiment of the inventive concept, there is no need to move cells out of an incubator or to put cells back into the incubator for staining and photographing.

As a result, the volume of equipment may be small and the execution time may be shortened upon performing a time series quantification method of a supravital dye uptake of a cell, thereby maximizing the throughput of the quantification method.

Moreover, the absorbance of a process in which the supravital dye is injected and a sample cell is stained may be derived in a time-series manner.

Figure 17:
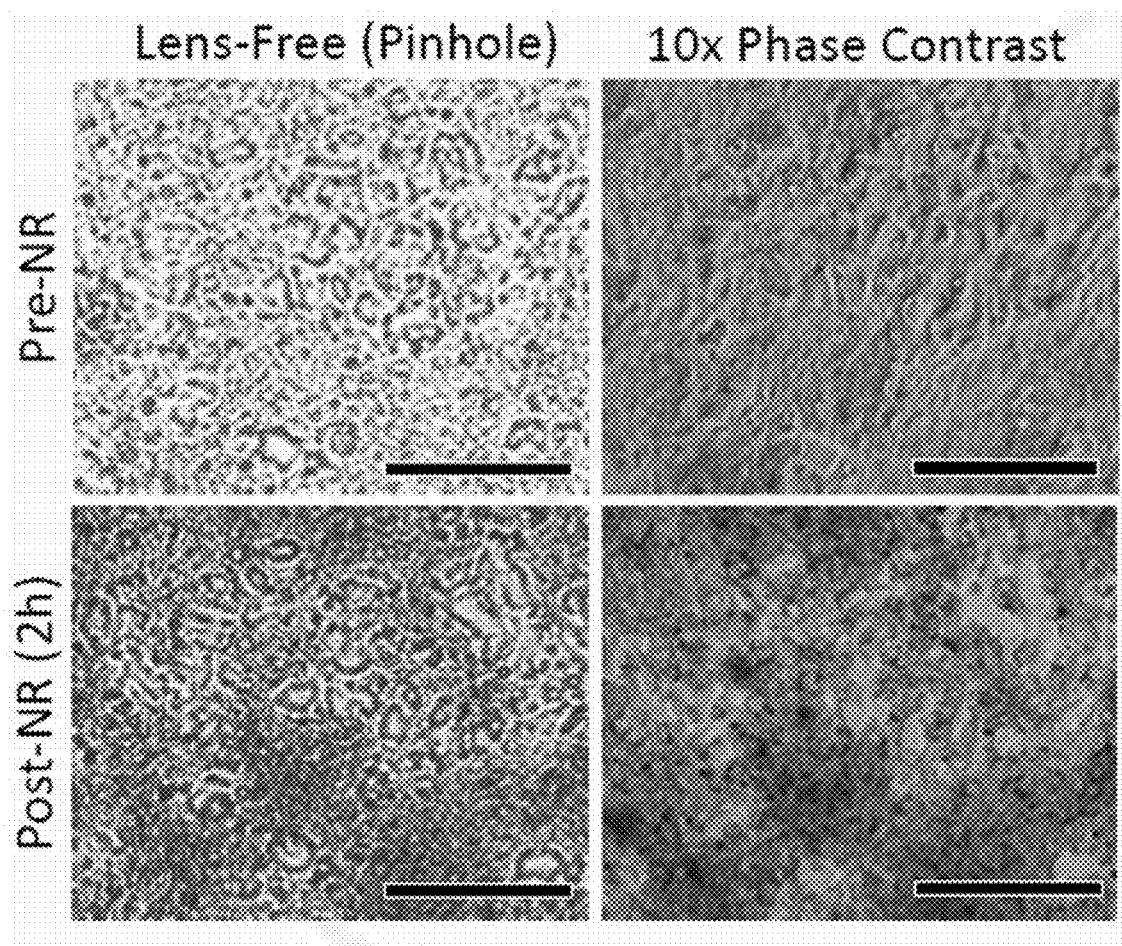
FIG. 17 is a diagram illustrating an image detected by a conventional optical microscope and an image detected by a lens-free imaging system of the inventive concept.

Also, referring to FIG. 17, an image detected by a conventional optical microscope 1 (right) and an image detected by the lens-free imaging system 100 (left) of the inventive concept are illustrated.

The image of a sample cell before the supravital dye is supplied is displayed on the upper side. The image of the stained sample cell after 2 hours later after the supravital dye is supplied is displayed on the lower side.

The lens-free imaging system 100 according to an embodiment of the inventive concept specify a boundary region, using pinhole illumination, and thus the perimeter of a sample cell may be specified relatively clearly. As a result, the reliability of the calculated absorbance may be improved.

Furthermore, according to an embodiment of the inventive concept, the extent to which sample cells overlap with one another may be derived using the difference in absorbance. Accordingly, it is possible to relatively easily derive a 3D image. The method according to an embodiment of the inventive concept may be implemented by a program (or an application) and may be stored in a medium such that the program is executed in combination with a server being hardware.

The above-described program may include a code encoded by using a computer language such as C, C++, JAVA, a machine language, or the like, which a processor (CPU) of the computer may read through the device interface of the computer, such that the computer reads the program and performs the methods implemented with the program. The code may include a functional code related to a function that defines necessary functions that execute the method, and the functions may include an execution procedure related control code necessary for the processor of the computer to execute the functions in its procedures. Further, the code may further include additional information that is necessary for the processor of the computer to execute the functions or a memory reference related code on which location (address) of an internal or external memory of the computer should be referenced by the media. Moreover, when the processor of the computer needs to communicate with any other remote computer or any other remote server to perform the functions, the code may further include a communication-related code associated with how to communicate with any other remote computer or server using the communication module of the computer, what information or media should be transmitted or received during communication, or the like.

The stored medium refers not to a medium, such as a register, a cache, or a memory, which stores data for a short time but to a medium that stores data semi-permanently and is read by a device. Specifically, for example, the stored media include, but are not limited to, ROM, RAM, CD-ROM, magnetic tape, floppy disk, optical data storage device, and the like. That is, the program may be stored in various recording media on various servers that the computer can access, or various recording media on the computer of the user. In addition, the media may be distributed to a computer system connected to a network, and a computer-readable code may be stored in a distributed manner.

The steps of a method or algorithm described in connection with the embodiments of the inventive concept may be embodied directly in hardware, in a software module executed by hardware, or in a combination thereof. The software module may reside on a Random Access Memory (RAM), a Read Only Memory (ROM), an Erasable Programmable ROM (EPROM), an Electrically Erasable Programmable ROM (EEPROM), a Flash memory, a hard disk, a removable disk, a CD-ROM, or a computer readable recording medium in any form known in the art to which the inventive concept pertains.

Although embodiments of the inventive concept have been described herein with reference to accompanying drawings, it should be understood by those skilled in the art that the inventive concept may be embodied in other specific forms without departing from the spirit or essential features thereof. Therefore, the above-described embodiments are exemplary in all aspects, and should be construed not to be restrictive.

According to an exemplary embodiment of the inventive concept, the absorbance of the sample cells may be quantified without a destructive post-treatment procedure for sample cells. As a result, the time required to quantify absorbance may be shortened.

Besides, because a lens-free image sensor is used, the volume of equipment required to quantify the absorbance may be reduced relatively. As a result, the process of quantifying the absorbance may be performed more conveniently and efficiently.

Furthermore, at each moment in a process of incubating and staining a sample cell, the absorbance of the sample cell may be quantified in real time.

In addition, the overlap degree of sample cells may be derived based on the relative difference in absorbance, and thus the 3D image of the sample cell may be derived relatively easily.

The effects of the present inventive concept are not limited to the aforementioned effects, and other effects not mentioned herein will be clearly understood from the following description by those skilled in the art to which the inventive concept pertains.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A real-time quantification method of cell viability through a supravital dye uptake using a lens-free imaging system, the method comprising:
   incubating a sample cell in a cell culture medium;
   detecting, by a lens-free image sensor included in the lens-free imaging system, light penetrating the cell culture medium, and identifying a boundary region of the sample cell at a preset time interval based on the detected light;
   staining the incubated sample cell with the supravital dye;
   detecting, by the lens-free image sensor, intensity of light penetrating the cell culture medium at a preset time interval;
   calculating absorbance of the sample cell included in the cell culture medium at a preset time interval based on the boundary region and the detected intensity of light;
   classifying a portion, in which the absorbance is not greater than a preset value, in a portion of the boundary region as a non-overlapping region;
   classifying a portion, in which the absorbance is greater than the preset value, in a portion of the boundary region as an overlapping region; and
   analyzing, by the lens-free imaging system, a viability of the sample cell based on the calculated absorbance, the non-overlapping region, and the overlapping region,
   wherein the identifying comprises:
      detecting, by the lens-free image sensor, the light penetrating the cell culture medium; and
      distinguishing the boundary region of the sample cell based on the detected light,
   wherein the identifying is performed while a light source, a pinhole filter through which a pinhole capable of penetrating light is formed, the cell culture medium, and the lens-free image sensor are arranged sequentially,
   wherein the distinguishing of the boundary region comprises:
      receiving a shadow image of the sample cell detected by the lens-free image sensor;
      specifying the boundary region of the sample cell based on the received shadow image; and
      specifying coordinates of a pixel of the lens-free image sensor, corresponding to the boundary region of the sample cell, and
   wherein the calculating comprises:
      when the boundary region is detected as 'n' individual regions separated from each other, calculating the light intensity for each of the 'n' individual regions; and
      calculating the absorbance for each pixel of the lens-free image sensor,
   wherein the analyzing comprises:
      correcting the viability of the sample cell based on an overlap degree of the overlapping region, wherein the viability of the sample cell included in the overlapping region is multiplied by $\frac{1}{2}$ as a correction value for the overlapping region having two cells, which are overlap with each other, and wherein the overlap degree of the overlapping region is calculated based on the absorbance of the overlapping region.

2. The method of claim 1, wherein the detecting of the intensity of light is performed while a light source, a collimator configured to convert incident light into collimated light, the cell culture medium, and the lens-free image sensor are arranged sequentially.

3. The method of claim 2, wherein the detecting of the intensity of light includes:
- detecting, by the lens-free image sensor, first light intensity, which is intensity of light penetrating an inside of the boundary region; and
- detecting, by the lens-free image sensor, second light intensity, which is intensity of light penetrating an outside of the boundary region.

4. The method of claim 3, wherein the calculating includes:
- calculating the absorbance based on a ratio of the first light intensity to the second light intensity.

5. The method of claim 4, wherein the absorbance decreases as the ratio of the first light intensity to the second light intensity increases, and increases as the ratio of the first light intensity to the second light intensity decreases.

6. The method of claim 1, wherein the distinguishing of the boundary region includes:
- classifying a region including an oblong boundary in the boundary region and having an internal area not greater than a preset first area, as the non-overlapping region; and
- classifying a region including a circular boundary in the boundary region and having the internal area not greater than a preset second area, as the overlapping region, and wherein the first area is greater than the second area.

7. The method of claim 1, wherein the incubating, the staining, and the analyzing are performed while the lens-free imaging system including the cell culture medium is arranged inside an incubator of a preset environmental condition.

8. A non-transitory computer readable medium, to be combined with a computer, which is hardware, the non-transitory computer readable medium storing a program to perform the method of claim 1.

* * * * *